United States Patent
Birkenbach et al.

(10) Patent No.: US 7,294,106 B2
(45) Date of Patent: *Nov. 13, 2007

(54) CABLE-FREE MEDICAL DETECTION AND TREATMENT SYSTEM

(75) Inventors: Rainer Birkenbach, Poing (DE); Günter Müller, Markt Schwaben (DE)

(73) Assignee: BrainLAB AG, Feldkirchen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/922,046

(22) Filed: Aug. 19, 2004

(65) Prior Publication Data

US 2005/0033161 A1   Feb. 10, 2005

Related U.S. Application Data

(63) Continuation of application No. 09/999,247, filed on Nov. 1, 2001, now Pat. No. 6,782,285.

(30) Foreign Application Priority Data

Dec. 21, 2000  (EP) .................. 00127951

(51) Int. Cl.
*A61B 5/00*  (2006.01)
(52) U.S. Cl. ............... 600/300; 600/101; 600/407; 600/424; 600/437; 128/903; 128/920; 345/7
(58) Field of Classification Search ......... 128/903, 128/904, 920; 600/101, 300, 407, 424, 427, 600/437, 439; 345/7, 8
See application file for complete search history.

(56) References Cited

U.S. PATENT DOCUMENTS

| 5,027,825 | A | 7/1991 | Phelps et al. |
|---|---|---|---|
| 5,335,249 | A * | 8/1994 | Krueger et al. ............. 375/149 |
| 5,383,454 | A | 1/1995 | Bucholz |
| 5,389,101 | A | 2/1995 | Heilbrun et al. |
| 5,494,034 | A | 2/1996 | Schlöndorff et al. |
| 5,517,990 | A | 5/1996 | Kalfas et al. |
| 5,603,318 | A | 2/1997 | Heilbrun et al. |
| 5,622,170 | A | 4/1997 | Schulz |
| 5,643,268 | A | 7/1997 | Vilsmeier et al. |

(Continued)

FOREIGN PATENT DOCUMENTS

WO   94/13197   6/1994

(Continued)

OTHER PUBLICATIONS

Debros F. et al. "Wireless Data Communication: Example of an Application for the Operating Room". Computing and Monitoring in Anesthesia and Intensive Care. Recent Technological Advances, Hamamatsu, Japan, Apr. 1991.

(Continued)

*Primary Examiner*—Ruth S. Smith
(74) *Attorney, Agent, or Firm*—Renner, Otto, Boiselle and Sklar, LLP

(57) ABSTRACT

A system for medical detection and treatment comprising a number of treatment and/or detection devices which exchange data with each other within the context of a medical treatment, in particular a surgical or radiotherapeutic and/or radiosurgical operation, wherein the data are exchanged via radio interfaces in and/or on the devices.

14 Claims, 1 Drawing Sheet

U.S. PATENT DOCUMENTS

| | | |
|---|---|---|
| 5,662,111 A | 9/1997 | Cosman |
| 5,767,791 A | 6/1998 | Stoop et al. |
| 5,776,064 A | 7/1998 | Kalfas et al. |
| 5,817,005 A | 10/1998 | Cohen |
| 5,820,553 A | 10/1998 | Hughes |
| 5,836,954 A | 11/1998 | Heilbrun et al. |
| 5,851,183 A | 12/1998 | Bucholz |
| 6,050,724 A | 4/2000 | Schmitz et al. |
| 6,093,146 A | 7/2000 | Filangeri |
| 6,119,033 A | 9/2000 | Spigelman et al. |
| 6,351,659 B1 | 2/2002 | Vilsmeier |
| 6,406,426 B1 * | 6/2002 | Reuss et al. ................ 600/300 |
| 6,561,978 B1 | 5/2003 | Conn et al. |
| 6,608,688 B1 * | 8/2003 | Faul et al. .................. 356/614 |
| 6,735,630 B1 * | 5/2004 | Gelvin et al. ............... 709/224 |
| 2002/0111545 A1 | 8/2002 | Lindberg et al. |
| 2006/0220784 A1 * | 10/2006 | Wang et al. ............... 340/3.54 |

FOREIGN PATENT DOCUMENTS

| | | |
|---|---|---|
| WO | 00/36974 | 6/2000 |
| WO | 00/53115 | 9/2000 |

OTHER PUBLICATIONS

John S. Gage, M.D.; "Catching the Wave Breakthroughs in Wireless Technology", *MD Computing*, Mar./Apr. 1999.

* cited by examiner

CABLE-FREE MEDICAL DETECTION AND TREATMENT SYSTEM

This application is a continuation of U.S. patent application Ser. No. 09/999,247 filed on Nov. 1, 2001, now U.S. Pat. No. 6,782,285, which is hereby incorporated herein by reference in its entirety.

TECHNICAL FIELD

The present invention relates to a system for medical detection and treatment comprising a number of treatment and/or detection devices which exchange data with each other within the context of a medical treatment, in particular a surgical or radiotherapeutic and/or radiosurgical operation.

DESCRIPTION OF RELATED ART

In the course of technical advancement, it is becoming increasingly important, even in the area of medicine, for treatment and/or detection devices to exchange data with each other. In this way, a number of devices already now co-operate under computer guidance by means of data exchange, for example in an operating room, when the operation is assisted by a medical navigation and tracking system. In this respect, position data for example, or data concerning the current status of the patient, are detected (for example by cameras or inter-operative imaging methods such as for example intra-operative nuclear spin tomographs and/or computer tomographs) and these data are delivered to a central computational and guidance unit, which after computer-assisted processing outputs treatment-assisting and/or treatment-guiding information on a screen for the physician carrying out the treatment. As it often occurs that a multitude of such treatment devices are used, and these devices exchange their data via cable connections in accordance with the prior art, there is more often than not an accumulation of laid cables which disrupt the physicians carrying out the treatment and the support staff, or restrict their freedom of movement. The cabling means that a few of the devices have to be placed very near to the patient bed, which further restricts freedom of movement. The situation is made even worse by the fact that said devices essentially require an electric power supply, and for this reason even more cable has to be laid. Moreover, installing the devices in the operating room is very costly due to the necessity of laying a large number of cables, for which reason technical support staff have to work for a long time in preparation.

Sources of errors arise if connections are inadvertently damaged, or if they corrode, or if other contact problems arise, and individual treatment devices, for example ultrasound probes, can scarcely be packed sterilely, since they hang by the cable connection.

SUMMARY OF THE INVENTION

It is therefore the object of the present invention to provide a system for medical detection and treatment comprising a number of treatment and/or detection devices which overcomes the above disadvantages of the prior art. In particular, the system is to optimise the connection of devices for data exchange. Secure data transfer is also to be ensured, and specifically the freedom of movement of the operating team is to be improved.

This object is solved in accordance with the invention by a system for medical detection and treatment comprising a number of treatment and/or detection devices which exchange data with each other within the context of a medical treatment, in particular a surgical or radiotherapeutic and/or radiosurgical operation, wherein said data are exchanged via radio interfaces in and/or on the devices. In other words, a cable-free system is provided with respect to data exchange, which has the major advantage that the cables which were previously required for data exchange are now no longer present in the operating room and also cannot therefore disrupt. Since such systems can in principle easily overcome the distances obtaining in an operation room, there advantageously exists the further possibility of placing all devices which do not necessarily have to be present in the vicinity of the patient bed at a distance from it, such that they do not obstruct. Apparatus for treatment and/or treatment-assisting apparatus can be placed at the most suitable locations, easily and regardless of cable lengths, and can even be hung from the ceiling. Moreover, the handling of hand-held devices or probes is no longer impeded by disruptive data transfer cables.

The enclosed sub-claims define preferred embodiments of the present invention.

In this way, radio transmission is possible over short distances within a treatment room in an ISM (industrial, scientific, medical) band, and at low energy, in particular around 1 mW, in the high-frequency range, in particular in a range around 2.4 GHz (ISM band), in particular at 2.4 GHz to 2.4835 GHz (blue tooth band), or alternatively in the 900 MHz ISM band and/or in the ISM band from 5.150 to 5.875 GHz. Thus, international standards (blue tooth standard, hyperLAN) which are especially suitable for application with the present invention are available, among others, for such radio transmission.

One or more of the following devices may be equipped, within the framework of the present invention, with radio interfaces for communicating:

- a camera system, in particular an infrared camera system, for example for use with a medical navigation and tracking system;
- an audio means, for example for use with a medical navigation and tracking system;
- a video means, in particular a screen and a video-signal generating device, also head-mounted displays, for example for use with a medical navigation and tracking system;
- a microscope means, for example for use with a medical navigation and tracking system;
- an ultrasound detecting means and/or a means for processing detected ultrasound signals, for example for use with a medical navigation and tracking system;
- robots, in particular medical robots, for example for use with a medical navigation and tracking system;
- patient bearings, in particular patient beds, for example for use with a medical navigation and tracking system;
- imaging devices, in particular medical imaging devices, preferably for detecting volume data sets, such as tomographs, for example for use, including intra-operatively, with a medical navigation and tracking system;
- AGV devices (Automatic Guided Vehicles; driverless transport systems);
- apparatus and instruments for treatment, in particular medical and/or surgical instruments, for example for use with a medical navigation and tracking system;
- endoscopes;
- C-arc x-ray device and/or fluoroscopy devices.

For the devices cited above, the possibility of optimally placing or arranging them in the treatment and/or operation room is to be emphasised, and other advantages also arise. For example, instruments for treatment, such as probes for example, can be designed as "intelligent" probes which transmit data concerning their current location or status or the location or status of the detected structures via their interfaces and an operating means (for example a type of mouse click). As far as the use of endoscopes is concerned, the cabling which, when using a miniature transmitter on the endoscopic probe, normally consists of an electric power supply, a light supply, and a line for sending video signals can be reduced by at least said latter video signal line, the possibility existing in principle of scaling down the endoscopic probes and their cable attachments and thus more easily and less invasively penetrating into previously inaccessible target volumes.

Advantageously, the devices can transfer data concerning their own identification and/or detected medical data and/or data concerning their own position or that of other objects. Transferring data for identifying the devices in particular makes the system very secure as compared to the prior art, since this rules out errors such as arise from defective cable connections. It is possible to carry out radio transmission for a device on a number of varying channels, until a channel is found which allows the data to be transferred sufficiently accurately, which improves the overall security of the data transfer. In this way, the sender and receiver search for a suitable channel until the optimal preconditions for data transfer are created. The coding can be varied, which ensures that the devices are correctly assigned. An identification key for each transmitter ensures straight away that the communication signals are assigned to the correct devices from the start.

In an advantageous embodiment of the system in accordance with the invention, said system comprises a central, computer-assisted receiving, sending and evaluating unit which carries out recognition, regulation and control routines based on the exchanged data, and transmits evaluated data. A computer is suitable in this respect, such as is for example already currently used within the framework of computer-assisted navigation and tracking systems, wherein said computer advantageously no longer has to be placed directly by the patient bed, but can stand to one side in the operating room. Overall, the cable-free medical detection and treatment system is particularly suitable for being integrated into a medical navigation and tracking system comprising the corresponding treatment means.

A further major advantage with respect to freedom of movement and reducing the number of cable connections to be provided and/or laid out emerges if the devices are driven by accumulators or batteries, as in accordance with a preferred embodiment of the present invention. Since some of the devices used in such treatment require an electrical power supply, electrical power supply cables are conventionally also necessary to operate them, said cables having the disruptive effect already described. Within the context of the advancement in battery and accumulator technology, it is in principle possible within the framework of the invention to eliminate even these power connections and to provide devices which complete data exchange without cables and use their own power supply. Using this measure, a cable-free operation room can be substantially provided. By omitting cables, disinfection measures can be significantly simplified, and electrical interfaces with delicate plug contacts—which are likewise difficult or impossible to clean—may be omitted. In technical terms, this increases operational safety and simultaneously saves on costs, since costly insulating measures using optical couplers, transmitters etc. as well as ESD protective circuits, for example, may be omitted.

The devices, exchanging data without cables, can be accommodated in a single treatment and operating room. There is, however, also the possibility of providing a radio linking means between a number of rooms and to have the devices, accommodated in different rooms, exchange data without cables, in this way. Thus, for example, a nuclear spin tomograph placed in a separate room can be constantly provided with up-to-date data on the condition of the patient, in particular the up-to-date anatomy of the patient, and directly used under the correct conditions, even if the patient has to be taken to another room during or after the operation, for a control tomograph.

Transmitting video and image signals could possibly become difficult due to the large quantity of data to be transmitted. The present invention offers a number of solutions in this respect. For example, a means can be inserted for compressing the video or image signal data. The possibility also exists of providing a means for converting digital video or image signals into data signals of a small volume, for example composite signals, and it is furthermore possible within the framework of the present invention to split up the video or image signals using a suitable means and to transmit them portion by portion in parallel, in particular using multi-channel RF transmission connections.

DETAILED DESCRIPTION OF THE INVENTION

Figure 1:
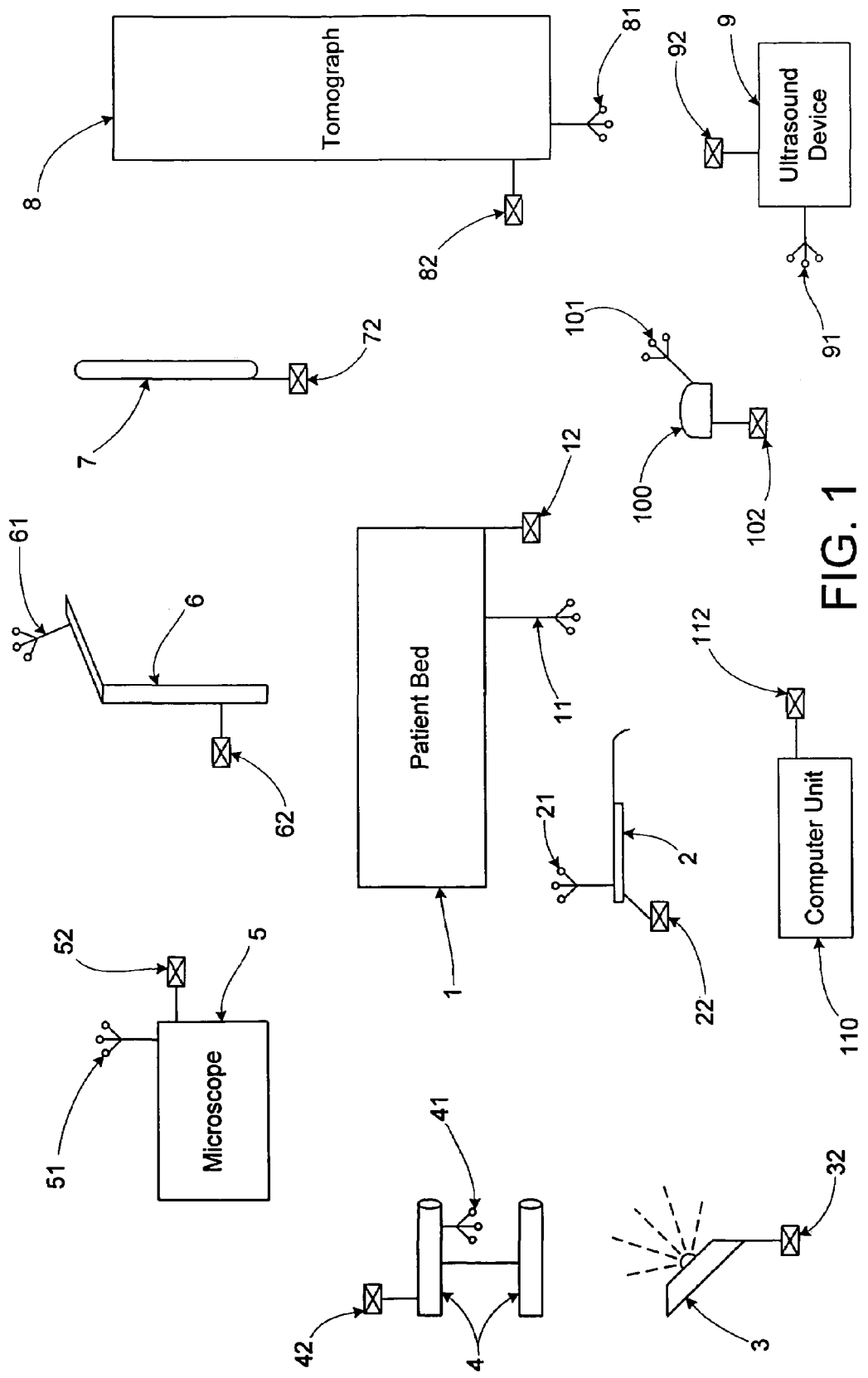
FIG. 1 shows a schematic overview of an operating room comprising a plurality of treatment and/or detection devices.

In the following, the invention will be explained in more detail by way of an example embodiment with the aid of the enclosed drawing. The drawing shows a schematic overview over an operating room comprising treatment and detection devices placed in it. A patient bed 1, a probe 2, which here stands in general for instruments for treatment, such as probes, forceps, scalpels, etc., an infrared light emitter 3, an infrared camera system 4, a surgical microscope 5, a surgical robot 6, a screen 7 as video-support for treatment, an intra-operative nuclear spin tomograph 8 which is arranged portable in such a way that it can be moved over the patient bed 1, an ultrasound device 9 and a corresponding ultrasound probe 100, and a central computer unit 110 are provided in the operating room. Said latter computer unit 110 controls, regulates and processes the processes and information in the system, wherein it is also perfectly possible for individual devices from those cited above themselves comprise control and processing units for information.

In accordance with the invention, all the devices shown are equipped with radio interfaces, schematically represented by a small box, respectively designated by the reference number of the device followed by a 2. Thus, the patient bed 1 has a radio interface with the reference number 12, the probe 2 has a radio interface with the reference number 22, etc. Except for the computer 110 and the infrared emitter 3, all the devices or device units shown are also provided with reference markers which allow the navigation and tracking system consisting of these reference markers, the camera system 4, the infrared emitter 3 and the computer 110, to detect and track the spatial position of the devices in the operating room and thus to enable navigation- and image-assisted treatment. Reference markers and/or arrangements of reference markers (adapters are respectively shown schematically, with three markers on each device) are provided with the reference number of the respective device followed by a 1, thus for example the patient bed 1 bears the arrangement of markers 11, the probe 2 bears the arrangement of markers 21, etc.

Navigating, which in this case is based on infrared-reflecting arrangements of markers and a corresponding camera system 4 comprising an infrared emitter 3, is known in principle and will only be briefly explained here. The arrangements of markers on the respective devices reflect the light from source of infrared light 3, and the corresponding reflection signals received by the cameras of the camera system 4 are evaluated, such that the spatial position of any one of the devices provided with an arrangement of markers can be determined. The computer co-ordinates this information and uses it to output an image support on the screen 7. For this purpose alone, it used to be at least necessary for cable connections to exist between from the screen 7 to the computer 110, and for the camera system 4, the computer 110 and the screen 7 to be fixed, together with the source of infrared light 3, to a single stand, and in a way which allowed the position of these parts to be clearly determined.

The present invention, in which data are now exchanged via the radio interfaces 112, 32, 42 and 72, brings considerable advantages, for this partial system alone, since the individual components no longer have to be provided together on one stand near the patient bed 1, rather the possibility exists in principle of relocating the components out of the area around the patient bed, and as far as possible in specially suited positions. Thus, for example, the camera system 4 can be fixed, together with the infrared light emitter 3, to the ceiling of the operating room, the computer 110 can easily be moved to the wall of the treatment room, and the screen 7 can be attached, for example, from the ceiling by a mounting, exactly where the physician carrying out the treatment can see it particularly well. The use of larger wall screens or projectors is also possible in principle. The aforementioned components of the navigation and tracking system can therefore be easily attached in such a way that they in no way disturb the physician or the operating team, and moreover still occupy an optimal place according to their function.

The above applies in principle to all the devices and instruments arranged in an operating room, and the units cited above, which may be used within the context of an operation, are also additionally shown in the drawing. Thus, the surgical microscope 5 also bears an interface 52. It can remain far from the patient bed while it is not needed, and then simply brought cable-free to the patient bed when it is to be used. Its position in the navigation system is then determined via the arrangement of markers 51, and the data detected by the microscope can be transmitted via the interface 52 to the computer 110, which then transmits the required image signals via its interface 112 to the screen 7 and its interface 72. The above also applies in principle to the treatment robot 6 and the intra-operative nuclear spin tomography system 8 which are both integrated in the navigation and tracking system and operate on the basis of up-to-date data and/or detect said up-to-date data.

Another radio-linked detection device is the ultrasound device 9 comprising the arrangement of markers 91 and the radio interface 92, as well as the corresponding ultrasound probe 100 comprising the arrangement of markers 101 and the interface 102. Due to the radio interface 102, by which the probe 100 can exchange data with the ultrasound device 9, said probe is particularly easy to handle, since a cable no longer needs to be provided for data exchange. Like all the other devices shown, the ultrasound probe can be accumulator- or battery-driven, which provides the additional advantage that in principle no more cable is required at all. In the case of the ultrasound probe 100, this means that the physician can move said probe completely freely, and can even sterilize it intra-operatively. It is conceivable to connect all the devices shown to docking stations before and after use, said stations re-charging the accumulators such that every device may be used over a long period of time from the beginning of the operation, without requiring a power cable supply. Interim solutions are also possible, since devices which can be rigidly mounted, such as for example the camera system 4 and the screen 7, can be provided with power via ceiling wires, without creating obstacles for the operating team.

Lastly, reference should be made to the possibility of also providing the probe 2 with a radio interface. This would lead to a sort of "intelligent" probe which can serve to detect the current position. The spatial position of the tip of the probe is known at any time via the arrangement of markers 21 in the navigation system. If the physician then guides the tip to a point on the patient's body, which itself can only be detected with difficulty in the navigation system, he can output a kind of "mouse click"—for example via a switch (not shown) on the probe 2. This signal would be registered by the computer 110, and it could then be positively established that the point on the body of the patient, on which the tip of the probe is resting, is situated at the moment of the mouse click in a defined spatial position. This is especially advantageous when body structures change during an operation, for example the brain when the cranium is opened or when a lesion is removed.

Artificial markers on the patient can of course also be re-registered using the aforementioned method.

Data for identifying the respective devices, detected medical data, data concerning the position of given objects or other objects, or combinations of these may be transmitted via the radio interfaces, as well as other relevant data.

The invention claimed is:

1. A system for medical detection and/or treatment during a medical procedure, comprising a number of medical treatment and/or detection devices each equipped with a wireless transmission interface, and at least two of the treatment and/or detection devices being configured to establish two-way communications with one-another so as to exchange non-tracking data via the wireless transmission interface, said data including medical data and information identifying the device from which the data is transmitted, whereby the data can be correlated to the device from which it originated, wherein the wireless transmission interface includes a radio interface that transmits at an energy level of less than about 1 mW.

2. A system as set forth in claim 1, further comprising a medical navigation and tracking system, and wherein at least one device is trackable by the medical navigation and tracking system.

3. A system as set forth in claim 2, wherein said at least one devices is equipped with an arrangement of reference markers for enabling tracking of the respective device's spatial position in an operating room by the medical navigation and tracking system.

4. A system as set forth in claim 1, wherein one of the devices includes a probe whose status can change, and the data includes information regarding the status of the probe.

5. A system as set forth in claim 4, wherein the probe includes a switch, and the data includes the status of the switch.

6. A system as set forth in claim 1, wherein the number of devices includes one or more of a camera system, a video display, a head-mounted display, a microscope means, an imaging device, a robot, a patient bed, a transport device, an endoscope, and a surgical instrument.

7. A system as set forth in claim 1, comprising a computer-assisted receiving, sending and evaluating unit that carries out recognition regulation and control routines based on the exchanged data, and transmits evaluated data.

8. A system as set forth in claim 1, wherein said treatment and/or detection devices are operable to directly exchange data with one another.

9. A system as set forth in claim 1, wherein said treatment and/or detection devices are operable to exchange data with one another through an intermediary device.

10. The system of claim 1, wherein said medical data includes configuration data for configuring the medical treatment and/or detection devices and/or patient data collectable during a medical procedure.

11. A system for medical detection and/or treatment in an operating room, comprising:
a plurality of medical devices each including a wireless communications interface, and at least one of the medical devices including a trackable device for enabling the location of said one medical device in three-dimensional space to be tracked by a medical navigation and tracking system, wherein said at least one and another of the medical devices are operable to establish two-way communications with one another so as to exchange at least non-tracking data, said data including medical data, wherein the wireless communications interface includes a radio interface that transmits at an energy level of less than about 1 mW.

12. A system as set forth in claim 11, wherein said communications includes an identifier that enables each respective communication message to be correlated to the device from which it originated.

13. A system as set forth in claim 11, further comprising a controller operative to coordinate communications between the plurality of medical devices.

14. The system of claim 11, wherein said medical data includes configuration data for configuring the medical treatment and/or detection devices and/or patient data collectable during a medical procedure.

* * * * *